US007423278B2

(12) United States Patent
Amaldi et al.

(10) Patent No.: US 7,423,278 B2

(45) Date of Patent: Sep. 9, 2008

(54) ION ACCELERATION SYSTEM FOR HADRONTHERAPY

(75) Inventors: Ugo Amaldi, Geneva (CH); Massimo Crescenti, Geneva (CH); Riccardo Zennaro, Versoix (CH)

(73) Assignee: Fondazione per Adroterapia Oncologica-TERA, Novara (NO) (IT)

( * ) Notice: Subject to any disclaimer, the term of this patent is extended or adjusted under 35 U.S.C. 154(b) by 365 days.

(21) Appl. No.: 11/232,929

(22) Filed: Sep. 23, 2005

(65) Prior Publication Data

US 2006/0170381 A1 Aug. 3, 2006

(30) Foreign Application Priority Data

Feb. 2, 2005 (IT) .......................... CO2005A0007

(51) Int. Cl.
*A61N 5/00* (2006.01)

(52) U.S. Cl. .................... 250/492.3; 315/500; 315/502; 315/505

(58) Field of Classification Search .............. 250/492.3; 315/500, 502, 505
See application file for complete search history.

(56) References Cited

U.S. PATENT DOCUMENTS

| | | | | |
|---|---|---|---|---|
| 2004/0108823 A1* | 6/2004 | Amaldi et al. | .............. | 315/505 |
| 2007/0108922 A1* | 5/2007 | Amaldi | ....................... | 315/502 |

OTHER PUBLICATIONS

Amaldi, U. et al., "LIBO—a linac-booster for protontherapy: construction and tests of a prototype", Nuclear Instruments & Methods in Physics Research, Elsevier Netherlands, vol. 521, No. 2-3, Apr. 1, 2004, pp. 512-529, XP-002375468.

Kim, J. et al., "Design Study of a Superconducting Cyclotron for Heavy Ion Therapy", AIP Conference Proceedings AIP USA, No. 600, 2001, pp. 324,326, XP-002378388.

Nolen, J., "Overview of Linac Applications at Future Radioactive Beam Facilities", Proceedings of the XVIII International Linear Accelerator Conference Cern Geneva, Switzerland, vol. 1, 1996, pp. 32-36, XP-008062524.

Chen, Z. et al., "Bridge Coupler Thermal/Structural Analysis and Frequency Shift Studies for the Coupled Cavity Linear Accelerator of the Spallation Neutron Source", Particle Accelerator Conference, 2001, IEEE Piscataway, NJ, USA, vol. 2, pp. 897-899, XP-002375469.

(Continued)

*Primary Examiner*—Jack I. Berman
*Assistant Examiner*—Michael Maskell
(74) *Attorney, Agent, or Firm*—Young & Thompson

(57) ABSTRACT

System for ion acceleration for medical purposes comprising a conventional or superconducting cyclotron, a radiofrequency linear accelerator (Linac), a Medium Energy Beam Transport line (MEBT) connected, at the low energy side, to the exit of the cyclotron, and at the other side, to the entrance of the linear radiofrequency accelerator, as well as a High Energy Beam Transport line (HEBT) connected at high energy side to the radiofrequency linear accelerator exit and at the other end, to a system for the dose distribution to the patient.

The high frequency of operation of the Linac allows for a reduced consumption and a remarkable compactness facilitating its installation in hospital structures. The use of a modular LINAC allows varying in active way the energy and the current of the therapeutic beam, having a small emittance and a time structure adapted to the dose distribution based on the technique known as the "spot scanning".

20 Claims, 2 Drawing Sheets

OTHER PUBLICATIONS

Nolen, J., "Radioactive beam facilities of North America", Nuclear Physics, Elsevier Netherlands, vol. 746, Dec. 27, 2004, pp. 9-16, XP-002375470.

Fietier, N. et al., "High Intensity Cyclotrons for Driving Hybrid Nuclear Systems", International Conference on Cyclotrons and Their Applications, Jun. 14, 1998, pp. 389-392, XP-008010909.

* cited by examiner

ION ACCELERATION SYSTEM FOR HADRONTHERAPY

FIELD OF THE INVENTION

The present invention relates to a ion acceleration system for hadronthrapy according to the preamble of claim 1, and more precisely to a beam acceleration system for either nuclei (e.g. $^{12}C^{6+}$) or molecules (e.g. $H^{+}_{2}$) with a mass number higher than 1, henceforth named "ions", for example for medical use in hadrontherapy.

BACKGROUND OF THE INVENTION

As known, hadrontherapy is the therapeutic technique that uses beams either of protons or heavier charged particles with mass number higher than 1.

It is equally known that in protontherapy, that is that particular hadrontherapy technique based on the use of proton beams, therapeutic beams of relatively low current (of the order of some nanoamperes) are used, with energies in the range 60 to 250 MeV, and a velocity interval between about 25% and 62% of the velocity of light.

It is also observed that in the case of different ions, therapeutic beams with lower currents and higher energies are required compared to the ones for the protons. For example, in the case of carbon ions $^{12}C^{6+}$, the required energies are between about 1.500 and 4.800 MeV (about 120 e 400 MeV/u). For a generic ion the interesting energies are from 50 to 500 MeV/u, corresponding to velocities between 15% and 75% of the velocity of light.

In the field of protontherapy among the different types of existing accelerators both cyclotrons (conventional or superconducting) and synchrotrons are used. The use of linear accelerators (Linac) has also been proposed.

The mass of the cyclotron magnet increases with the mass number and with the energy of the accelerated ions and becomes very large when one intends to cover the whole range of the energies needed for the therapy with carbon and similar ions. In particular today there are no hadrontherapy hospital centers based on cyclotrons accelerating carbon ions to the maximum energy of about 5000 MeV. Therefore special synchrotrons are used, adjusted for such a therapy and, unlike the cyclotrons, they have the extra advantage of producing variable energy ion beams.

However, hadrontherapy centers equipped with a synchrotron are extremely complex as they require a high number of high technology equipments derived from the technology of particle accelerators. In addition these centers are quite large, also due to the surface occupied by the synchrotron, and they require high investments and large installation surfaces that are not always available in the hospitals neighborhoods.

It is also acknowledged that the most advanced radiotherapy requires beams of composite charged particles (either totally or partially ionized nuclei or molecules) with mass number greater than 1, of quite low intensity (less than a few nanoampere). Such a requirement does not hold in the in the field of particle accelerators; physicists indeed need high currents for their experiments. This simplification, typical of the medical use, adds up to the requirement for the highest possible compactness of the system, as it ought to be installed in a hospital environment.

SUMMARY OF THE INVENTION

The basic aim of the present invention is to propose a system for ion acceleration for hadrontherapy that eliminates the inconveniences of the known techniques, and that is able to vary the energy and the (small) current of the therapeutic beam in an active way, minimizing construction costs and installation volume.

The indicated task is performed thanks to an ion accelerating system for hadrontherapy featuring the characteristics of claim #1.

Further favorable developments of the invention can be pointed out in the deriving claims.

The use of the ion acceleration system for hadrontherapy according to the invention presents many important advantages. First of all is the reduction of complexity, in comparison with known systems, as this is a modular structure, with a simple beam time structure (that is with no complex time cycles typical of synchrotrons) and composed of the same high technology equipment that repeats almost without variation for each module. Secondly, by adding further components similar to those already installed, the maximum operation energy can be increased even in a second time, after the construction of the accelerator. Furthermore the proposed system is relatively compact, so minimal volumes and installation surfaces are obtained, therefore facilitating the installation in hospital centers. Moreover, the high frequency of the Linac allows for reduction of power consumption which reflects in reduced exploitation costs.

A further and important advantage of the invention is that it provides a system with a built-in accelerator where energy and current of the therapeutic beam can be varied easily and continuously in an active way. This last property is indeed also present in a synchrotron, although with higher complexity and error margins.

It is also underlined that commonly the quality of a Linac output beam is better in dimension and divergence compared with those of the synchrotrons and also of the cyclotrons. Since the emittances of the produced therapeutic beam are lower than those produced by the other accelerators, the mass and cost of the magnetic channels for beam transport, in particular for the rotating gantries used for the treatments, are reduced.

One more advantage should be recognized in the time structure of the therapeutic beam which is well suited to treatments using the technique of the "spot scanning", as in use, for instance, at the PSI Center (Paul Scherrer Institute, CH-5232 Villigen, Switzerland).

The Linac, disclosed in the WO 2004/054331 and in U.S. Ser. No. 10/602,060 by the Requestor, can be used as the high frequency modular Linac, and its content is hereby included for reference.

BRIEF DESCRIPTION OF THE DRAWINGS

Further advantages, details and characteristics of the ion acceleration system for hadrontherapy according to the invention will furthermore result from the following description of a preferred pattern of execution of the invention, schematically illustrated in the appended Figures.

SUMMARY OF THE INVENTION

System for ion acceleration for medical purposes comprising a conventional or superconducting cyclotron, a radiofrequency linear accelerator (Linac), a Medium Energy Beam Transport line (MEBT) connected, at the low energy side, to the exit of the cyclotron, and at the other side, to the entrance of the linear radiofrequency accelerator, as well as a High Energy Beam Transport line (HEBT) connected at high energy side to the radiofrequency linear accelerator exit and at the other end, to a system for the dose distribution to the patient.

The high frequency of operation of the Linac allows for a reduced consumption and a remarkable compactness facilitating its installation in hospital structures. The use of a modular LINAC allows varying in active way the energy and the current of the therapeutic beam, having a small emittance and a time structure adapted to the dose distribution based on the technique known as the "spot scanning".

(FIG. 1)

DETAILED DESCRIPTION OF PREFERRED EMBODIMENTS

Figure 1:
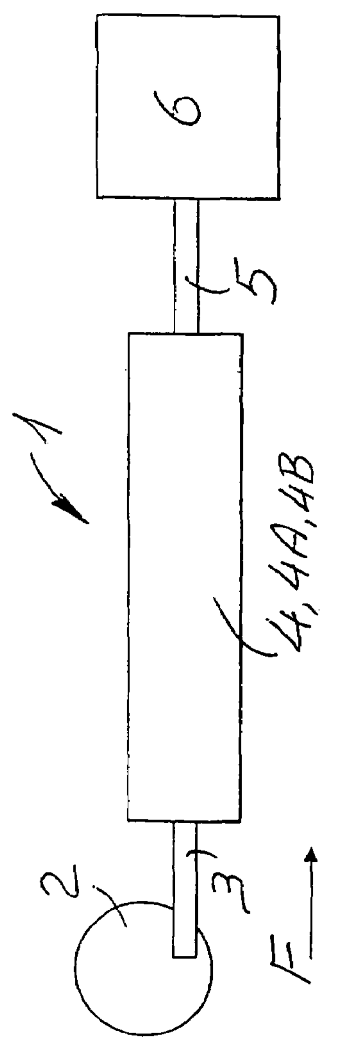
FIG. 1 and FIG. 3 show a block diagram of two possible versions of a ion acceleration system for hadrontherapy according to the invention.
Figure 2:
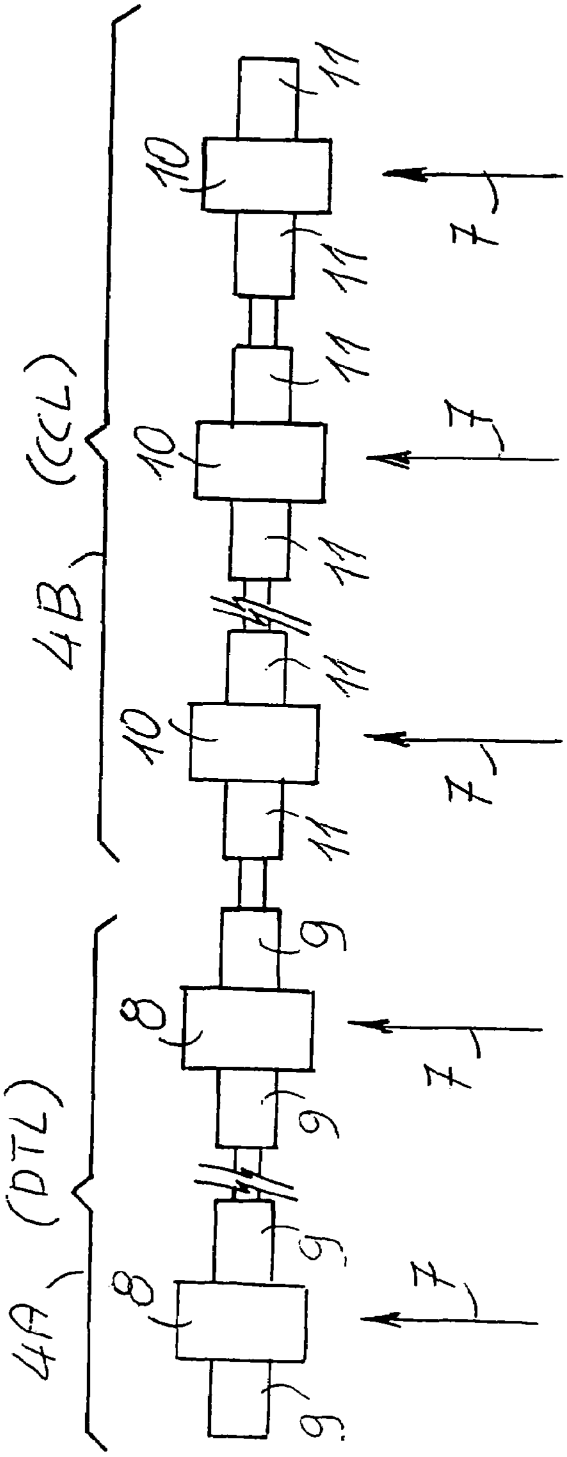
FIG. 2 shows an example of execution of a modular Linac in a block diagram.
Figure 3:
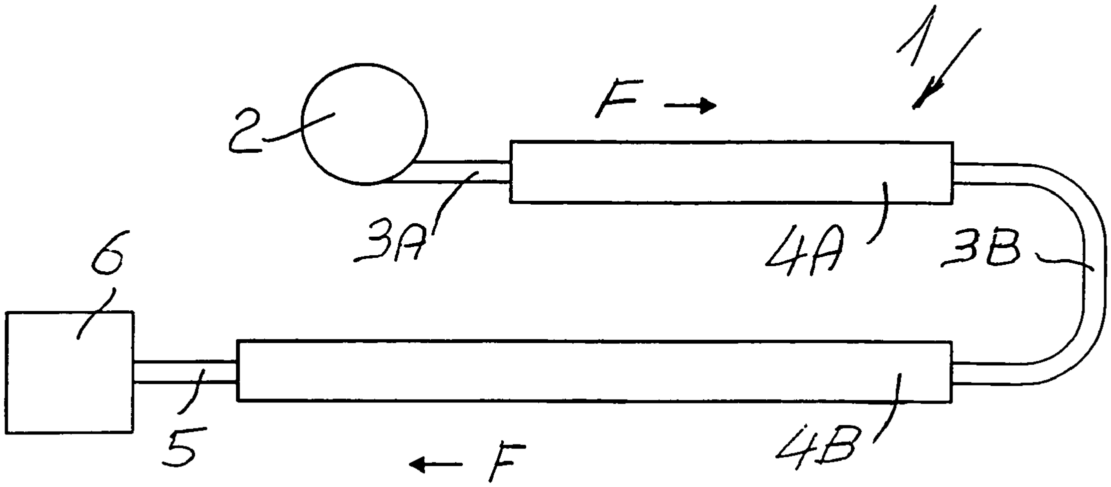

The components of the system according to the invention illustrated in FIGS. 1, 2 and 3 are the following:

1 Ion acceleration system for hadrontherapy;
2 Cyclotron;
3 Medium Energy Beam Transfer line (MEBT);
3A Medium-low Energy Beam Transfer line;
3B Medium-high Energy Beam Transfer line;
4 Modular Linac at high frequency, typically higher than 1 GHz;
4A Modular Linac 4 DTL accelerating section whose number of modules depends on the application;
4B Modular Linac 4 CCL accelerating section whose number of modules depends on the application;
5 High Energy Beam Transport line (HEBT);
6 Area for beam utilization;
7 Power inputs;
8 Modules of the accelerating section of the DTL structure;
9 Single accelerating section of the DTL structure;
10 Modules of the accelerating section of the CCL structure;
11 Single accelerating section of the CCL structure;
F Beam direction.

As from FIG. 1, the ion acceleration system for hadrontherapy 1 according to the invention includes mainly two different accelerating machines 2 and 4 arranged in series, and more precisely a cyclotron 2 and a modular Linac 4, of the type, for instance, of the one published in the WO2004/054331 and in the U.S. Ser. No. 10/602,060.

The Cyclotron 2 could be either conventional or superconducting when higher energies are required, or whenever the dimensions and costs of the magnet, which is an essential part of the machine, impose such a choice. The output energy of the Cyclotron 2 is normally fixed and its value will be established at each time by the application, specifically depending on the type of hadrontherapy center to develop and/or on the kind of therapy to perform. Cyclotron 2 may be fed by an external or internal source of particles (not shown), and the output beam can be continuous or modulated at the repetition frequency of the Linac. The extraction system foreseen could allow the simultaneous production of several beams from the Cyclotron 2, some of which can be used directly for other purposes, as for instance, the production of radioisotopes for diagnostic and/or therapeutic purposes.

One or more beams at the exit of the Cyclotron 2 pass through a coupling section or Medium Energy Beam Transfer line (MEBT) 3, in which magnetic lenses and a current control device, well known and hereby not shown, allow the injection with enough efficiency in the Linac 4.

The linac radiofrequency technology is currently used for charged particles acceleration exiting from an "ion source" up to the desired energy. According to the invention the Linac 4 is used as a post-accelerator downstream of the Cyclotron 2 for atomic or composite nuclear particles of mass number higher than 1 and with charge different than 0.

The energy (velocity) range covered by the Linac 4 spans from the output energy (velocity) of the Cyclotron 2 to a maximum energy that depends on the therapy. In order to define-this maximum energy one commonly uses the $\beta$ parameter, defined as the ratio between the velocity of the particle and the velocity of light. A minimum of about 10 MeV/u (Mega or millions of electronvolt per nucleon) and a maximum of about 300 MeV/u for the input energy of the Linac 4 are therefore requested (that is, corresponding to the exit energy of the Cyclotron 2), while the exit energy of the Linac 4, that is the energy required for the therapy, lies in the range of about 50 MeV/u and 500 MeV/u, globally corresponding to $0.15 \leqq \beta \leqq 0.75$.

The above values typically lay in the field of standing wave linacs. In standing wave structures, the accelerator is a resonant cavity inside which oscillating electric fields result by excitation of the cavity electromagnetic field resonating modes.

In order to optimize the accelerating field and minimize power consumption, different types of structures are employed each of them very efficient only in a particular and reduced velocity interval.

According to the invention, if the injector Cyclotron 2 was a low energy one and the maximum energy limit was required, this could be reached by dividing the Linac 4 in two Linacs 4A and 4B with different characteristics, namely, the Linac 4A would be a Drift Tube Linac (DTL), or a Side-Coupled Drift Tube Linac (SCDTL) and Linac 4B, serially coupled, would be a Coupled Cavity Linac (CCL). Both mentioned Linac 4A and 4B are built from many coupled cavities and foresee many RF power input, indicated with the arrows 7. The single modules, for instance of the DTL structure and their relative accelerating sections are shown respectively with 8 and 9, while the single modules of the CCL structure and their relative accelerating sections are respectively indicated with 10 and 11. The output energy of the Linac 4B beam may be modulated by varying the RF frequency input of the last modules. The intensity of the Linac 4B output beam may be modulated by varying the parameters and the beam dynamics of the beam injected by the Cyclotron 2 into the Linac 4A.

According to the invention it is foreseen to minimize the installed power of the Linac 4 by changing the structure at the energy where the DTL or SCDTL 4A consumes more than the CCL 4B, that is at about 100 MeV/u ($\beta \approx 0.4$).

According to the invention it is moreover possible to extend the use of the CCL 4B to lower energies, or analogously of the DTL or SCDTL 4A to higher energies, in order to use one linac typology alone to avoid rising the cost and/or the complexity of the system.

Else, if the particular therapeutic application and/or the input energy allow it, one single typology can simply be used.

Concerning the DTL 4A, according to the invention one can use a structure working in the transverse electric (TE) field mode, also named H mode, intrinsically more efficient at low energy than the transverse magnetic field mode (TM) also known as E mode. Instead, at higher energies the CCL 4B uses the TM mode, with better performances at such energies.

According to the invention it is foreseen to use a CLUSTER like structure (as per mentioned WO2004/054331 and U.S. Ser. No. 10/602,060) for the DTL 4A or else a SCDTL (Side-Coupled Drift Tube Linac) structure where, as known, small DTL structures working in the TM mode are coupled together.

According to the invention it is foreseen a high frequency CCL 4B of the Side-Coupled type, with characteristics similar to the ones of a proton accelerator already successfully experimented and disclosed by the Requestor in the field of protontherapy.

According to the invention the efficiency and compactness of system 1 increases by using a working frequency equal to or higher than 1 GHz, unusual for conventional linacs. Indeed, the higher the frequency, the higher the achievable field, with consequently increase of energy gain per meter and reduction of the total length of the accelerator. This is a very critical issue in medical applications, where the attempt to reduce the total length of the accelerator is linked to the necessity of reducing costs and installation volumes. By adopting the high frequency as the invention proposes, a reduction in power consumption is advantageously obtained. In fact, as general rule, if the geometry of the structure is scaled with the frequency, the effective shunt impedance per unit of length, a parameter that is proportional to the acceleration efficiency, increases with the square root of the frequency.

The beam-hole diameter is smaller, but this is compatible with the low current required. This choice brings also the advantage of a better beam quality, in dimensions and divergence, of the Linac 4 output beam because only the central part of the phase space of the beam extracted from the Cyclotron 2 is accelerated, with respect to the quality that can be obtained by a cyclotron or a synchrotron. Therefore said output beam is better adapted to the therapeutic use, in particular in the case of an active dose distribution system.

The radiofrequency Linac 4 produces bunched beams of typically 5 microseconds every 5 milliseconds, with a duty cycle of 0.1%. The resulting pulsed time structure of the therapeutic beam can be used for treatments with active, as well as passive, dose distribution systems. It is particularly suitable, as mentioned earlier, for the "spot scanning" technique developed at the PSI laboratory.

It is worthwhile noticing here that the typical quality of the beam exiting from a cyclotron is very different from the one typically required by a radiofrequency linac. Indeed, as the frequency of the Cyclotron 2 is of the order of some tens of MHz, while the one of the Linac 4 is at least 1 GHz, the fraction of the accelerated particles is of the order of 10%.

Furthermore, considering a 0.1% duty cycle for the Linac, the global loss factor in the longitudinal plane is $10^4$. In the transversal plane, where the linac acceptance is usually less than the cyclotron emittance, the loss factor is not larger than 5. Therefore the loss factor at the interface cyclotron-linac is globally not larger than $5\times10^4$.

Despite all this, the current required for the therapy with ions with mass higher than 1 are very low. For instance, a current of some hundreds of picoampere (i.e. about $10^{-10}$ ampere) is required for carbon ions $^{12}C^{6+}$. Therefore, considering the loss factor, it is enough for the cyclotron to produce 5-10 microampere (i.e $5\text{-}10\times10^{-6}$ ampere) of $^{12}C^{6+}$ carbon ions, synchronized with the pulses of the Linac radiofrequency system (for instance at 200 Hz).

The functioning of the ion acceleration system for hadrontherapy 1 according to the invention can be resumed as follows:

The cyclotron 2, conventional or superconducting, pre-accelerates the ion beam to an intermediate energy. This pre-accelerated beam is then injected into a medium energy beam transport line (MEBT) 3, that focuses and transports the beam to the Linac 4 entrance, respectively 4A.

In the Linac 4 the accelerated beam is simultaneously accelerated and longitudinally focused by radiofrequency electric fields to the wanted energy. The transverse focusing is independently supplied by magnetic lenses, not shown. The Linac 4 shows a modular configuration as mentioned above. The radiofrequency power is distributed in an adjustable and independent way in each module 8, respectively 10. Consequently, the energy of the Linac 4 output beam, or 4B, is adjustable even during the same treatment. The two sections DTL (or SCTDT) 4A e CCL 4B may have the same or different frequencies.

At Linac 4 output, the ion beam is driven to a high energy beam transport line 5 (HEBT) that focuses and transports the beam to the area 6 for therapeutic use.

As illustrated above, according to the invention, the Linac 4 may be made of two different types of structures indicated with 4A and 4B. Each of these structures is optimally designed to work in its energy range, as indicated for instance in FIG. 2 for a Linac 4 structure composed of two DTL type modules 8 and three CCL type modules 10. One single type of structure could also be used whenever the therapy should require either a low energy, enough to allow the use of structure 4A alone, or whenever the cyclotron energy is high enough, typically higher than 100 MeV/u, where structure 4B alone could be used. Special cases may require more sections with different characteristics and (multiple) frequencies.

As an example, we show here three different implementations according to the invention.

The numerical values of the first two schemes are reported in Table 1. Both are based on the use of a conventional or superconducting cyclotron pre-accelerating a $^{12}C^{6+}$ carbon ion beam up to the energy of 300 MeV/u. This beam is then driven through a MEBT 3 transport line to a Linac 4, which in this case is only of the type SCL (Side-Coupled Linac) that accelerates the beam up to 400 MeV/u. The two schemes propose two Linacs 4 whose design frequencies are different: 2.988 GHz and 5.710 GHz. They may be powered by commercial radiofrequency amplifiers (klystron), as for example those produced by the company Thales Electron Devices (address: 2, bis rue Latecoere, 78941 Velizy Cedex, France).

For the transverse beam focusing, both schemes use very small commercial permanent quadrupole magnets, such that they can fit inside Linac 4, between two consecutive accelerating sections, forming an alternate focusing, FODO type, system.

TABLE 1

Two examples of possible Linac modules to accelerate $^{12}C^{6+}$ (Q = 6, A = 12)

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Diameter for an accelerating cell [mm] | 70 | 40 |
| Diameter of the beam pipe [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average Effective Shunt Impedance $ZT^2$ [MΩ/m] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |

TABLE 1-continued

| Two examples of possible Linac modules to accelerate $^{12}C^{6+}$ (Q = 6, A = 12) | | |
|---|---|---|
| Average power per module [kW] | 4.4 | 4.2 |
| Average power of the Linac [kW] | 44 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |
| Average quadrupole magnetic gradient B' [T/m] (in FODO configuration) | 160 | 320 |
| Normalized transverse acceptance, 1 rms [π mm mrad] | 1.8 | 1.4 |

The numerical values of the third scheme are presented in Table 2 and the layout showing positions of the various elements is shown in FIG. 3.

In this case, a conventional cyclotron 2 pre-accelerates the carbon $^{12}C^{6+}$ ion beam up to the energy of 50 MeV/u.

This beam is then driven through a beam transport line MEBT 3A to the first section of the Linac 4A of DTL type, that accelerates it to the energy of to 160 MeV/u. A second beam transport line MEBT 3B, in this case not straight, conveys the beam to the second Linac 4B section of SCL type, where the beam is further accelerated up to a maximum energy of 400 MeV/u.

Thanks to the use of magnetic dipoles in the MEBT 3B it is possible to bend and invert the beam direction F, so that the Linac sections 4A e 4B would be closely aligned, allowing for a valuable space reduction.

TABLE 2

| Third example of possible Linac modules to accelerate $^{12}C^{6+}$ (Q = 6, A = 12). | | |
|---|---|---|
| Linac type of structure | DTL | CCL |
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam hole diameter [mm] | 4 | 4 |
| Number of accelerating structures per module | 4 | 2 |
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad] | 0.8 | 0.9 |

From the structural and functional description of the ion acceleration system for hadrontherapy according to the invention, we can affirm that it allows to efficiently meet the purpose for which it was conceived and allows to obtain the mentioned advantages.

Experts in the field may introduce modifications and variations of structural or dimensional parts to adapt to specific cases without anyhow exiting the boundaries of the protection of the invention as described and claimed.

LITERATURE

List of some publications in the sector of hadrontherapy and related accelerators:

U. Amaldi and M. Silari (Eds.), "The TERA Project and the Centre for Oncological Hadrontherapy, Vol. I, Vol. II", INFN-LNF Divisione Ricerca ISBN 88-86409-09-5, I-00044 Frascati (Rome) Italy, April 1995. The "*Blue Book*".

U. Amaldi, M. Grandolfo, and L. Picardi editors, "The RITA Network and the Design of Compact Proton Accelerators", INFN-LNF Frascati, Italy, August 1996 (ISBN 88-86409-08-7). The "*Green Book*".

U. Amaldi (Ed.), "The National Centre for Oncological Hadrontherapy at Mirasole", INFN-LNF Divisione Ricerca ISBN 88-86409-29-X, I-00044 Frascati (Rome) Italy, February 1997. The "*Red Book*".

U. Amaldi et al., "A Linac-booster for Protontherapy: Construction and Tests of a Prototype", Nuclear Instruments and Methods in Physics Research A 521 (2004) 512-529.

M. Crescenti and 8 co-authors, "Proton-Ion Medical Machine Study (PIMMS) PART I", CERN/PS 99-010 (DI), Geneva, Switzerland, March 1999.

M. Crescenti and 13 co-authors, "Proton-Ion Medical Machine Study (PIMMS) PART II", CERN/PS 2000-007 (DR), Geneva, Switzerland, July 2000. In particular: Chapter II-7 Injection.

L. Picardi, C. Ronsivalle and B. Spataro, "*Design development of the SCDTL structure for the TOP Linac*" Nuclear Instruments and Methods in Physics Research A, 425, (1999) 8-22

Projet Etoile, rapport LYCEN 2002-01 (A,B,C) UCB-Lyon & DAPNIA-02-06, DSM, CEA Saclay (2002).

U. Amaldi and 5 co-authors, "Design of a Centre for Biologically Optimized Light Ion Therapy in Stockholm", Nuclear Instruments and Methods in Physics Research Section B, Volume 184, Issue 4, December 2001, Pages 569-588.

E. Takada et al., Proc. of the 13th Sympo.on Accel. Sci. and Tech., Osaka, Japan (2001) pp. 187-189 (HIMAC Project).

A. Itano, Proc. of the 13th Sympo.on Accel. Sci. and Tech., Osaka, Japan (2001) pp. 160-164 (HIBMC Project).

WO 2004/054331 and U.S. Ser. No. 10/602,060 "LINAC FOR ION BEAM ACCELERATION". Inventors: AMALDI Ugo, CRESCENTI Massimo, ZENNARO Riccardo.

The invention claimed is:

1. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the radiofrequency linear accelerator features a resonant frequency greater than or equal to 1 GHz, and in order to accelerate $^{12}C^{6+}$ carbon ions starting at 300 MeV/u the section CCL alone of said Linac is used with frequencies of 2.998 GHz or 5.710 GHz and for which are included the following parameters respectively:

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Accelerating cell diameter [mm] | 70 | 40 |
| Beam hole aperture diameter [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average effective shunt impedance $ZT^2$ [MΩ/m] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |
| Average power per module [kW] | 4.4 | 4.2 |
| Average power of the Linac [kW] | 44 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |
| Average quadrupole magnetic gradient B' [T/m] (in FODO configuration) | 160 | 320 |
| Normalized transverse acceptance, 1 rms [π mm mrad] | 1.8 | 1.4. |

2. Acceleration system for composite charged particles of claim 1, configured for medical purposes.

3. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the radiofrequency linear accelerator features a resonant frequency greater than or equal to 1 GHz, and in order to accelerate $^{12}C^{6+}$ carbon ions, for the said Linac DTL section at a frequency of 2.855 GHz e and for the said Linac CCL section at a frequency of 5.710 GHz the following parameters are included:

| | | |
|---|---|---|
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam aperture diameter [mm] | 4 | 4 |
| Number of accelerating structures per module | 4 | 2 |
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad]. | 0.8 | 0.9 |

4. Acceleration system for composite charged particles of claim 3, configured for medical purposes.

5. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, and in order to accelerate $^{12}C^{6+}$ carbon ions starting at 300 MeV/u the section CCL alone of said Linac is used with frequencies of 2.998 GHz or 5.710 GHz and for which are included the following parameters respectively:

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Accelerating cell diameter [mm] | 70 | 40 |
| Beam hole aperture diameter [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average effective shunt impedance $ZT^2$ [MΩ/m] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |
| Average power per module [kW] | 4.4 | 4.2 |
| Average power of the Linac [kW] | 4.4 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |

-continued

| | | |
|---|---|---|
| Average quadrupole magnetic gradient B' [T/m] (in FODO configuration) | 160 | 320 |
| Normalized transverse acceptance, 1 rms [π mm mrad] | 1.8 | 1.4. |

6. Acceleration system for composite charged particles of claim 5, configured for medical purposes.

7. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, in said radiofrequency Linac, the DTL type and CCL type structures include a number of modules, and in order to accelerate $^{12}C^{6+}$ carbon ions starting at 300 MeV/u the section CCL alone of said Linac is used with frequencies of 2.998 GHz or 5.710 GHz and for which are included the following parameters respectively:

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Accelerating cell diameter [mm] | 70 | 40 |
| Beam hole aperture diameter [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average effective shunt impedance $ZT^2$ [MΩ/m] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |
| Average power per module [kW] | 4.4 | 4.2 |
| Average power of the Linac [kW] | 44 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |
| Average quadrupole magnetic gradient B' [T/m] (in FODO configuration) | 160 | 320 |
| Normalized transverse acceptance, 1 rms [π mm mrad] | 1.8 | 1.4. |

8. Acceleration system for composite charged particles of claim 7, configured for medical purposes.

9. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the conventional or superconducting cyclotron pre-accelerates the ion beam up to a fixed energy that can vary between about 10 and about 300 MeV/u, and in order to accelerate $^{12}C^{6+}$ carbon ions starting at 300 MeV/u the section CCL alone of said Linac is used with frequencies of 2.998 GHz or 5.710 GHz and for which are included the following parameters respectively:

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Accelerating cell diameter [mm] | 70 | 40 |
| Beam hole aperture diameter [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average effective shunt impedance $ZT^2$ [M Ω/m] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |
| Average power per module [kW] | 4.4 | 4.2 |
| Average power of the Linac [kW] | 44 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |
| Average quadrupole magnetic gradient B' [T/m] (in FODO configuration) | 160 | 320 |
| Normalized transverse acceptance, 1 rms [π mm mrad] | 1.8 | 1.4. |

10. Acceleration system for composite charged particles of claim 9, configured for medical purposes, and wherein, the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, and the two said Linac sections DTL and CCL have either the same frequency, either about 3 GHz or about 5.7 GHz, or different ones, respectively about 1.5 and about 3 GHz.

11. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, a high energy beam transport line (HEBT) connected, on one end to the output of said radiofrequency linear accelerator and on the other end to a system for dose distribution to the patient, and a source either continuous or pulsed in accordance to the Linac repetition rate, of the ECR, EBIS, or other source types, wherein, in order to accelerate $^{12}C^{6+}$ carbon ions starting at 300 MeV/u the section CCL alone of said Linac is used with frequencies of 2.998 GHz or 5.710 GHz and for which are included the following parameters respectively:

| | | |
|---|---|---|
| Frequency [MHz] | 2998 | 5710 |
| Q (ion charge) | 6 | 6 |
| A (ion mass) | 12 | 12 |
| Input Energy [MeV] | 3600 | 3600 |
| Output Energy [MeV] | 4800 | 4800 |
| Number of accelerating cells per accelerating structure | 20 | 13 |
| Accelerating cell diameter [mm] | 70 | 40 |
| Beam hole aperture diameter [mm] | 8 | 4 |
| Number of accelerating structures per module | 2 | 2 |
| Number of modules (same as the number of klystrons) | 10 | 16 |
| Average length of a module [m] | 1.8 | 0.72 |
| Total length of the Linac [m] | 17.8 | 11.5 |
| Average transit time factor T | 0.86 | 0.89 |
| Average effective shunt impedance $ZT^2$ [M Ωm] | 79 | 91 |
| Average electric field on axis $E_0$ [MV/m] | 17.8 | 31 |
| Maximum surface electric field in Kilpatrick units | 1.7 | 2.2 |
| Average peak power required per module [MW] | 4.4 | 4.2 |
| Average power per module [kW] | 4.4 | 4.2 |
| Average power of the Linac [kW] | 44 | 67.2 |
| Duty Factor [%] | 0.1 | 0.1 |
| Synchronous phase $\phi_s$ [degrees] | −15 | −15 |
| Magnetic quadrupole length [mm] | 52 | 60 |
| Magnetic quadrupole aperture diameter [mm] | 10 | 5 |
| Average quadrupole magnetic gradient B' [T/m] (in FODO configuration) | 160 | 320 |
| Normalized transverse acceptance, 1 rms [π mm mrad] | 1.8 | 1.4. |

12. Acceleration system for composite charged particles of claim 11, configured for medical purposes.

13. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, and in order to accelerate $^{12}C^{6+}$ carbon ions, for the said Linac DTL section at a frequency of 2.855 GHz e and for the said Linac CCL section at a frequency of 5.710 GHz the following parameters are included:

| | | |
|---|---|---|
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam aperture diameter [mm] | 4 | 4 |
| Number of accelerating structures per module | 4 | 2 |
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad]. | 0.8 | 0.9 |

14. Acceleration system for composite charged particles of claim 13, configured for medical purposes.

15. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and, a high energy beam transport line (HEBT) connected, on one end to the output of said radiofrequency linear accelerator and on the other end to a system for dose distribution to the patient, wherein, the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, in said radiofrequency Linac, the DTL type and CCL type structures include a number of modules, and in order to accelerate $^{12}C^{6+}$ carbon ions, for the said Linac DTL section at a frequency of 2.855 GHz e and for the said Linac CCL section at a frequency of 5.710 GHz the following parameters are included:

| | | |
|---|---|---|
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam hole aperture diameter [mm] | 4 | 4 |
| Number of accelerating structures per module | 4 | 2 |
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad]. | 0.8 | 0.9 |

16. Acceleration system for composite charged particles of claim 15, configured for medical purposes.

17. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, and a high energy beam transport line (HEBT) connected, on one end to the output of said radiofrequency linear accelerator and on the other end to a system for dose distribution to the patient, wherein, the conventional or superconducting cyclotron pre-accelerates the ion beam up to a fixed energy that can vary between about 10 and about 300 MeV/u, and in order to accelerate $^{12}C^{6+}$ carbon ions, for said Linac DTL section at a frequency of 2.855 GHz e and for the said Linac CCL section at a frequency of 5.710 GHz the following parameters are included:

| | | |
|---|---|---|
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam aperture diameter [mm] | 4 | 4 |
| Number of accelerating structures per module | 4 | 2 |
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad]. | 0.8 | 0.9 |

18. Acceleration system for composite charged particles of claim 17, configured for medical purposes, and wherein, the radiofrequency linear accelerator features a modular implementation and includes either a first accelerating structure section of DTL or SCDTL type and a following accelerating structure section of CCL type, or a single accelerating structure section type of DTL or SCDTL type, or a single accelerating structure section of CCL type, where the radiofrequency power in each module of which each section is composed is distributed in an adjustable and independent way, and the two said Linac sections DTL and CCL have either the same frequency, either about 3 GHz or about 5.7 GHz, or different ones, respectively about 1.5 and about 3 GHz.

19. Acceleration system for composite charged particles, nuclear or molecular, with mass number greater than 1, in the form of ion beams, comprising:

a conventional or superconducting cyclotron, a radiofrequency linear accelerator (Linac), a medium energy beam transport line (MEBT) connected, on one end, either to the cyclotron output or to the output of the first part of the radiofrequency linear accelerator and, on the other end, either to the input of the radiofrequency linear accelerator or to the second part of the said radiofrequency linear accelerator, a high energy beam transport line (HEBT) connected, on one end to the output of said radiofrequency linear accelerator and on the other end to a system for dose distribution to the patient, and a source either continuous or pulsed in accordance to the Linac repetition rate, of the ECR, EBIS, or other source types, wherein in order to accelerate $^{12}C^{6+}$ carbon ions, for the said Linac DTL section at a frequency of 2.855 GHz e and for the said Linac CCL section at a frequency of 5.710 GHz the following parameters are included:

| | | |
|---|---|---|
| Frequency [MHz] | 2855 | 5710 |
| Q (ion charge) | 6 | 6 |
| A (ion mass) | 12 | 12 |
| Input Energy [MeV] | 600 | 1920 |
| Output Energy [MeV] | 1920 | 4800 |
| Number of accelerating cells per accelerating structure | 7 | 14 |
| Accelerating cell diameter [mm] | 20 | 40 |
| Beam aperture diameter [mm] | 4 | 4 |
| Number of accelerating structures per module | 4 | 2 |

-continued

| | | |
|---|---|---|
| Number of modules (same as the number of klystrons) | 18 | 38 |
| Average length of a module [m] | 1.06 | 0.69 |
| Total length of the Linac [m] | 19.17 | 26.18 |
| Average transit time factor T | 0.86 | 0.89 |
| Average effective shunt impedance $ZT^2$ [MΩ/m] | 85 | 87 |
| Average electric field on axis $E_0$ [MV/m] | 24.3 | 32.2 |
| Maximum surface electric field in Kilpatrick units | 2.5 | 2.3 |
| Average peak power required per module [MW] | 3.5 | 4.8 |
| Average power per module [kW] | 3.5 | 4.8 |
| Average power of the Linac [kW] | 63 | 185 |
| Duty Factor [%] | 0.1 | 0.1 |
| Synchronous phase $\phi_s$ [degrees] | −14 | −15 |
| Magnetic quadrupole length [mm] | 60 | 60 |
| Magnetic quadrupole aperture diameter [mm] | 5 | 5 |
| Average quadrupole magnetic gradient B' [T/m] (in FODO configuration) | 250 | 240 |
| Normalized transverse acceptance, 1 rms [π mm mrad]. | 0.8 | 0.9 |

20. Acceleration system for composite charged particles of claim 19, configured for medical purposes.

* * * * *